(12) United States Patent
Mannheimer et al.

(10) Patent No.: US 8,364,221 B2
(45) Date of Patent: Jan. 29, 2013

(54) PATIENT MONITORING ALARM ESCALATION SYSTEM AND METHOD

(75) Inventors: Paul D. Mannheimer, Danville, CA (US); Li Li, Milpitas, CA (US); David A. Orian, Tracy, CA (US); J. Christopher Kilborn, Winnetka, IL (US)

(73) Assignee: Covidien LP, Mansfield, MA (US)

( * ) Notice: Subject to any disclaimer, the term of this patent is extended or adjusted under 35 U.S.C. 154(b) by 1041 days.

(21) Appl. No.: 12/276,188

(22) Filed: Nov. 21, 2008

(65) Prior Publication Data

US 2009/0221887 A1 Sep. 3, 2009

Related U.S. Application Data

(63) Continuation of application No. 11/241,513, filed on Sep. 30, 2005, now abandoned.

(51) Int. Cl.
*A61B 5/1455* (2006.01)
*G08B 23/00* (2006.01)

(52) U.S. Cl. .................................. 600/323; 340/573.1
(58) Field of Classification Search .................. 600/310, 600/322, 323; 340/573.1, 506, 507, 508
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |

(Continued)

FOREIGN PATENT DOCUMENTS

| CA | 2536290 | 8/2004 |
|---|---|---|
| JP | 2237544 | 9/1990 |

(Continued)

OTHER PUBLICATIONS

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

(Continued)

*Primary Examiner* — Eric Winakur

(57) ABSTRACT

Embodiments of the present invention relate to a patient monitoring alarm escalation system and method. Specifically, embodiments of the present invention include an alarm detection device configured to measure physiological data received via a patient monitor, the alarm detection device configured to initiate an alarm in response to predefined measurements of the physiological data, and an alarm device configured to emit a first signal with a first property and a second signal with a second property, the first signal being emitted when the alarm is initiated, the second signal being emitted if an alarm acknowledgement mechanism is not activated prior to a designated event.

25 Claims, 4 Drawing Sheets

U.S. PATENT DOCUMENTS

| | | |
|---|---|---|
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,652,566 A * | 7/1997 | Lambert ............ 340/507 |
| 5,680,857 A | 10/1997 | Pelikan et al. |
| 5,692,503 A | 12/1997 | Kuenstner |
| 5,730,124 A | 3/1998 | Yamauchi |
| 5,730,140 A * | 3/1998 | Fitch ............ 600/514 |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,027,453 A | 2/2000 | Miwa et al. |
| 6,027,455 A | 2/2000 | Inukai et al. |
| 6,036,651 A | 3/2000 | Inukai et al. |
| 6,036,652 A | 3/2000 | Inukai et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,398,727 B1 | 6/2002 | Bui et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,527,725 B1 | 3/2003 | Inukai et al. |
| 6,544,193 B2 | 4/2003 | Abreu |
| 6,546,267 B1 | 4/2003 | Sugiura et al. |
| 6,549,795 B1 | 4/2003 | Chance |
| 6,579,242 B2 | 6/2003 | Bui et al. |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,816,266 B2 | 11/2004 | Varshneya et al. |
| 6,829,496 B2 | 12/2004 | Nagai et al. |
| 6,830,549 B2 | 12/2004 | Bui et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,979,812 B2 | 12/2005 | Al-Ali |
| 6,983,178 B2 | 1/2006 | Fine et al. |
| 6,993,371 B2 | 1/2006 | Kiani et al. |
| 6,996,427 B2 | 2/2006 | Ali et al. |
| 7,006,865 B1 | 2/2006 | Cohen et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,079,036 B2 | 7/2006 | Cooper et al. |
| 7,107,096 B2 | 9/2006 | Fischell et al. |
| 7,123,950 B2 | 10/2006 | Mannheimer |
| 7,127,278 B2 | 10/2006 | Melker et al. |
| 7,162,306 B2 | 1/2007 | Caby et al. |
| 7,173,525 B2 | 2/2007 | Albert |
| 7,186,966 B2 | 3/2007 | Al-Ali |
| 7,209,775 B2 | 4/2007 | Bae et al. |
| 7,222,054 B2 | 5/2007 | Geva |
| 7,236,811 B2 | 6/2007 | Schmitt |
| 7,263,395 B2 | 8/2007 | Chan et al. |
| 7,272,426 B2 | 9/2007 | Schmid |
| 7,292,141 B2 | 11/2007 | Staats et al. |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2001/0045509 A1 | 11/2001 | Al-Ali |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |

| | | |
|---|---|---|
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0172222 A1 | 9/2004 | Simpson |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0267402 A1 | 12/2005 | Stewart et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0258926 A1 | 11/2006 | Ali et al. |
| 2007/0032714 A1 | 2/2007 | Mannheimer |
| 2007/0109115 A1 | 5/2007 | Kiana et al. |
| 2008/0183058 A1 | 7/2008 | Mannheimer |

FOREIGN PATENT DOCUMENTS

| | | |
|---|---|---|
| JP | 8256996 | 10/1996 |
| WO | WO 2004/038669 | 5/2004 |
| WO | WO 2005/020176 | 3/2005 |

OTHER PUBLICATIONS

Manley, Geoffrey t., et al., Cerebral Oxygenation during Hemorrhagic Shock: Perils of Hyperventilation and the Therapeutic Potential of Hypoventilation, Jun. 2000, The Journal of Trauma: Injury, Infection, and Critical Care, Lippincott Williams & Wilkins, Inc., 0022-5282/00/4806-1025.

Belal, Suliman Yousef, et al.; "A fuzzy system for detecting distorted plethysmogram pulses in neonates and paediatric patients," Physiol. Meas., vol. 22, pp. 397-412 (2001).

Lutter, Norbert O., et al.; "False Alarm Rates of Three Third-Generation Pulse Oximeters in PACU, ICU and IABP Patients," Anesth Analg, vol. 94, pp. S69-S75 (2002).

* cited by examiner

PATIENT MONITORING ALARM ESCALATION SYSTEM AND METHOD

This application is a continuation of U.S. application Ser. No. 11/241,513 filed Sep. 30, 2005, the disclosure of which is hereby incorporated by reference in its entirety.

BACKGROUND OF THE INVENTION

1. Field of the Invention

The present invention relates generally to alarm systems for patient physiological data monitoring instruments. In particular, the present invention relates to an alarm escalation system including mechanisms for indicating a level of criticality of alarms corresponding to physiological measurements and equipment status indicators of patient monitoring devices.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Patient monitors include medical devices that facilitate observation of patient physiological data. For example, a typical patient monitor detects and displays a patient's vital signs continually. This improves patient care by facilitating continuous supervision of a patient without continuous attendance by a human observer (e.g., a nurse or physician). Typically, patient monitors include alarm systems that provide audible and/or visual indications of certain predefined conditions. For example, some patient monitors include alarms that are triggered based on physiological conditions (e.g., high and low patient heart rate thresholds, arterial oxyhemoglobin saturation) or status indicators for the monitor itself (e.g., power loss). These alarms further facilitate supervision of patients and improve patient care by providing caregivers with warnings concerning certain monitored conditions. Generally, such alarms remain in an alarm state until acknowledged by a user. For example, an audible alarm for a patient's abnormal systolic condition may continue to sound until a user presses an acknowledge button that silences the alarm and indicates that the alarm has been recognized. Such audible alarms for patient monitors generally incorporate unchanging alarm tones or auditory effects. It is now recognized that such unchanging alarms tend to cause patient monitor users/operators (e.g., nurses, physicians, and caregivers) to become desensitized to ongoing and unacknowledged audible alarms.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
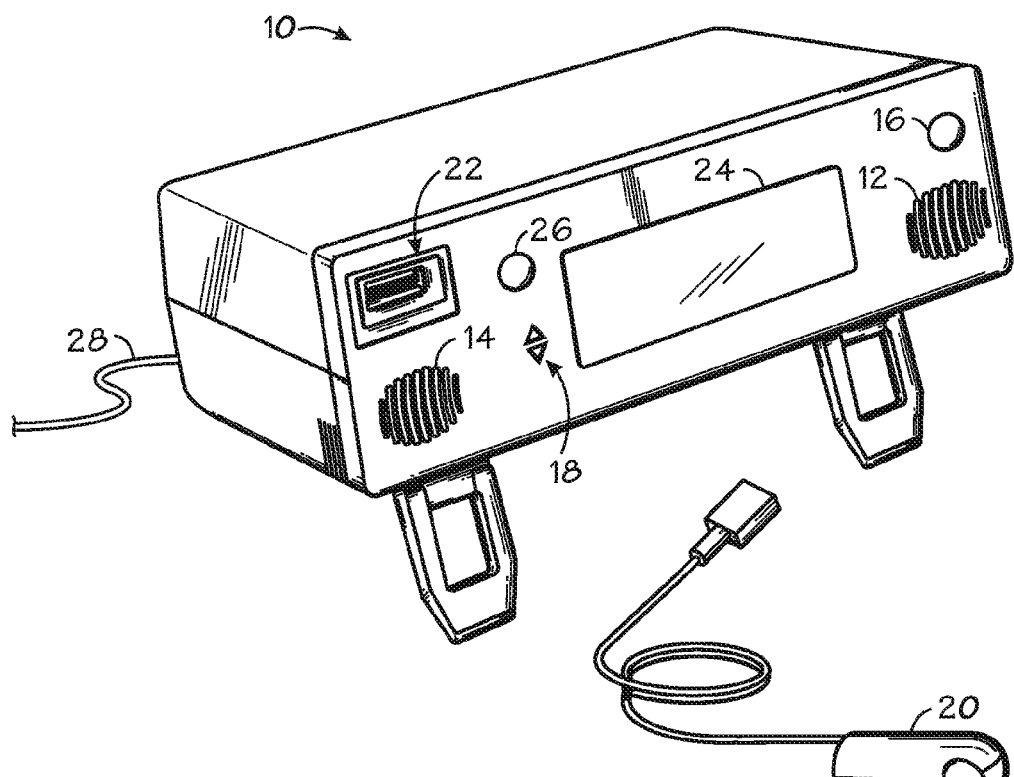
FIG. 1 is a perspective view of a patient monitor in accordance with an exemplary embodiment of the present invention.

FIG. 1 is a perspective view of a patient monitor in accordance with an exemplary embodiment of the present invention. Specifically, the patient monitor illustrated by FIG. 1 is a multi-speaker pulse oximeter 10 having a first speaker 12 and a second speaker 14. The pulse oximeter 10 may be configured to provide an active audible alarm with at least two distinctive tones. These distinctive tones may be utilized to elevate annoyance when an alarm condition remains unacknowledged for a certain period of time, thus directing a user's attention to the unacknowledged alarm condition. For example, in one embodiment, a first tone from the first speaker 12 is sounded in response to an alarm condition, and a second tone from the second speaker 14 is sounded as a reminder tone. The reminder tone is sounded after the alarm condition has remained unacknowledged for a designated amount of time. In another embodiment, distinctive reminder tones are sounded alternatively from the respective speakers 12 and 14, thus creating increasing audio agitation (e.g., increasing volume, frequency, and/or dissonance) after a designated amount of time has passed without the alarm condition having been acknowledged by pressing an alarm silence button 16. Additionally, the elevation of audio agitation may be accelerated the longer an alarm remains unacknowledged. For example, after the audio agitation has been increased a first time, the amount of time until it is increased again may be reduced by half and so forth.

In some embodiments, spatial separation of the first speaker 12 and the second speaker 14 may be used to increase alarm awareness among caregivers and to ensure that all areas of a room are accessible to an alarm. For example, stereo characteristics and so forth may be utilized to get the attention of a caregiver that is desensitized to typical alarms. In a specific example, the spatial separation of the first speaker 12 and second speaker 14 may be used to create unique sounds and/or to improve sound projection to all areas of a room. Further, embodiments of the present invention may be engineered to ensure that the location of the alarm device emitting the alarm is apparent to the caregiver. For example, if multiple devices are in a room, certain sound effects may be utilized to direct a caregiver's attention to the specific device that is emitting an alarm.

Alarm conditions are designated on the pulse oximeter 10 using set points or by designating patterns of values (e.g., patterns in an SpO2 trend) that can be entered via adjustment buttons 18. For example, a user can input a certain set point (e.g., 103 degrees Fahrenheit, blood oxygen level of 97%)

that creates an alarm condition when crossed by actual patient data (e.g., actual patient temperature, actual blood oxygen level), or when processed values or patterns of values are detected. The pulse oximeter 10 may detect alarm conditions using an alarm detection device that compares designated set points with actual patient data received from a sensor 20 via a cable connection port 22 that is configured to communicatively couple with the sensor 20. For example, in some embodiments, the alarm detection device employs SatSeconds™ by Nellcor™ to detect alarms and manage nuisance alarms. SatSeconds™ may include alarming based on an integral of time and depth of a desaturation event. The sensor 20 may be defined as an accessory used to collect and send patient data to the pulse oximeter 10. One end of the sensor 20 is typically coupled to a patient (e.g., to a patient's finger, toe, ear lobe, or forehead) and the other end couples either directly or indirectly (e.g., via a separate monitor cable) to the pulse oximeter 10. Exemplary sensors may include sensors available from Nellcor Puritan Bennett Incorporated. The sensor 20 in the illustrated embodiment couples with a patient's finger and is configured to collect patient physiological data by sensing a patient's pulse rate and percentage of oxygen in the arterial blood. Once collected, these measurements are sent to the pulse oximeter 10.

As set forth above, the pulse oximeter 10 illustrated by FIG. 1 includes dual speakers 12 and 14. The speakers 12 and 14 are configured to provide audible alarms based on certain detected conditions. For example, the speakers 12 and 14 may be utilized to produce audible alarms for detected conditions including: low battery, high or low oxygen saturation, high or low pulse rate, sensor disconnect, high patient temperature, high or low blood pressure, and so forth. While the embodiment illustrated by FIG. 1 includes a pair of speakers 12 and 14, other embodiments may include a single speaker, more than two speakers, or options relating to the provision of one or more speakers. Indeed, some embodiments include a monitor having connection points adapted to communicatively couple with a plurality of speakers. For example, a monitor in accordance with present embodiments may include one or more built-in speakers, expansion ports for coupling to one or more speakers, or both. Further, in some embodiments, remote speakers (e.g., pagers) may be utilized either with or without having speakers directly coupled to the pulse oximeter 10. It should be noted that in some embodiments, to utilize the connection points, external speakers are communicatively linked with the connection points and software on the oximeter 10 is updated to provide additional related functions.

Incorporating a plurality of speakers (e.g., speaker 12 and 14) with the pulse oximeter 10 provides versatility, redundancy, and reliability. For example, by emitting alarm tones and alarm reminder tones from multiple speakers, embodiments of the present invention can produce unique and recognizable alarm sounds that attract the attention of users by elevating annoyance levels of the alarm sounds. This versatility can increase the awareness of caregivers that may not respond quickly to standard alarms, resulting in improved response times and so forth. In a specific example, an alarm may sound from speaker 12 based on a blood pressure reading that passes a predefined alarm threshold. If this alarm is not acknowledged by, for example, pressing the alarm silence button 16, speaker 14 emits a secondary alarm having a different tone than the first alarm to further alert the caregiver of the alarm condition.

In addition to providing auditory versatility, having multiple speakers creates redundancy that improves reliability in the event of a speaker failure (e.g., a speaker being blocked and muffled by an object or a speaker with a faulty connection). Not all unacknowledged alarms will necessarily result from caregivers failing to hear or recognize the initial alarm. Indeed, an initial alarm may remain unacknowledged because a speaker assigned the task of emitting the initial alarm either failed to produce or failed to adequately emit the initial alarm tone. For example, if speaker 12 is configured to emit an initial alarm tone and speaker 14 is configured to emit a reminder alarm tone after the initial alarm is unacknowledged for a designated period, the reminder alarm tone provided by speaker 14 will serve as a back up alarm to alert the user of a pending alarm condition in the event speaker 12 fails to provide the initial alarm tone.

In another embodiment, both speakers 12 and 14 are essentially completely redundant. For example, in a completely redundant embodiment, all speakers (e.g., 12 and 14) are configured to emit the same alarm tones and alarm reminder tones based on the same measured conditions and unacknowledged alarms. If one speaker fails, at least one other speaker will have been redundantly assigned the same alarming task.

It should be noted that, in some embodiments, alarms are visually and/or haptically indicated in addition to being audibly indicated. Indeed, alarms may be indicated to alert any of a caregiver's senses (e.g., sight, touch, and hearing). These alternative sensory indications (e.g., alarm lights and vibrating pagers) are additional tools with which a user's attention can be directed to an alarm condition. For example, the pulse oximeter 10 includes a display 24, such as a liquid crystal display (LCD), that visibly displays alarm indications and other information. In one embodiment, the display 24 is configured to visually communicate patient physiological data (e.g., oxygen saturation percentage, pulse amplitude, pulse rate) and alarms in the form of numeric data, textual data, and/or graphical data (e.g., plethysmographic waveforms and/or alarm icons). The display 24 may also be configured to display equipment status indicators such as an on/off indication depending on whether a power button 26 in latched or unlatched, a power indication depending on whether a power cord 28 is receiving power, and/or other equipment status indicators. In one embodiment, the display 24 is used to visually confirm values entered while configuring aspects of the pulse oximeter 10 (e.g., providing set points for alarms via the adjustment buttons 18). It should also be noted that these extra indications provide supplemental redundancy.

Figure 2:
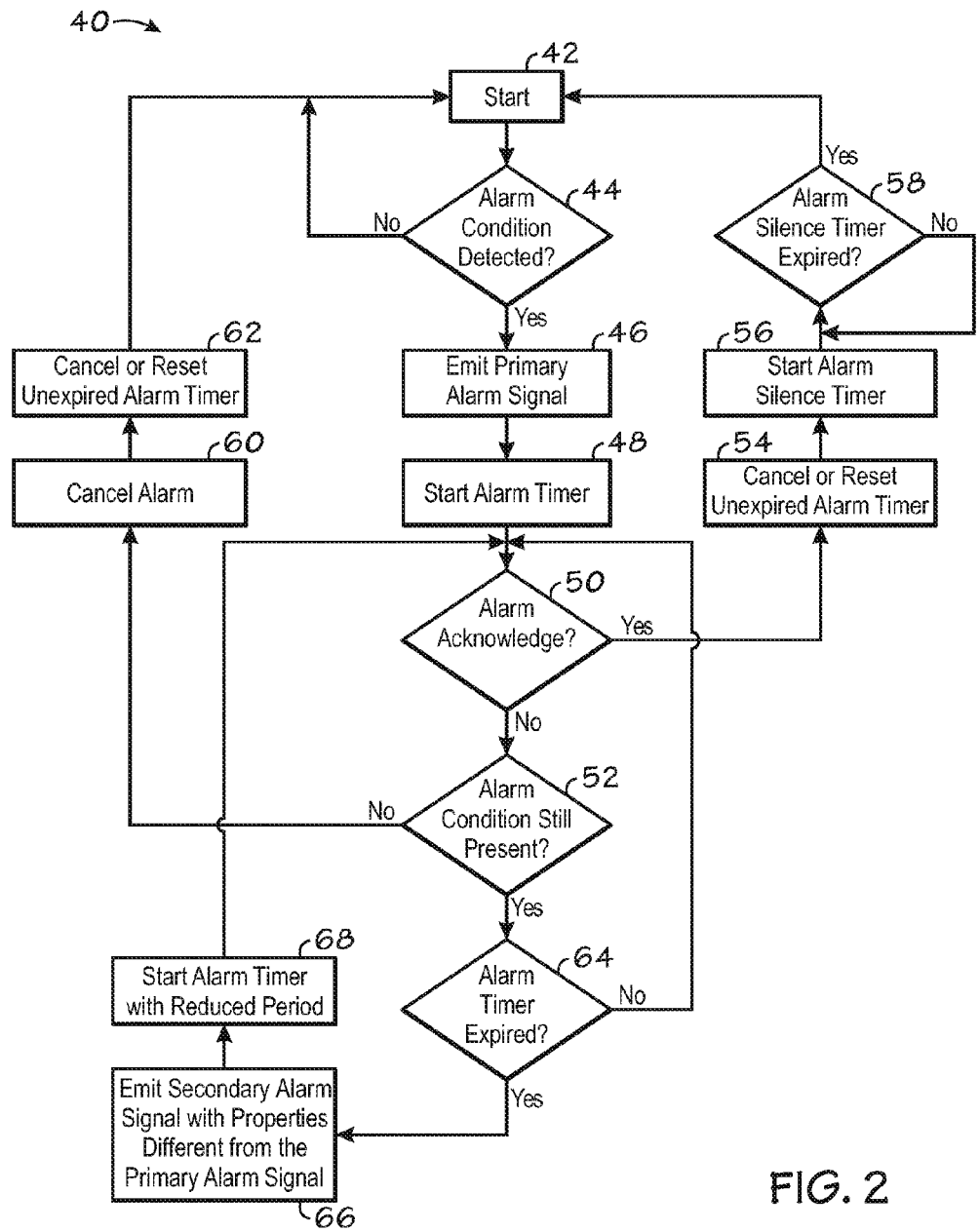
FIG. 2 is a block diagram of a method for providing patient monitor alarms in accordance with an exemplary embodiment of the present invention.

FIG. 2 is a block diagram of a method 40 for providing patient monitor alarms in accordance with an exemplary embodiment of the present invention. The method 40 can be implemented with a single alarm indicator or multiple alarm indicators. For example, embodiments of the present invention may use speakers, pagers, visual indicators, and/or haptic devices to provide the referenced signals (e.g., audible tones). The method 40 begins at block 42 and proceeds to block 44, which is a decision block regarding whether an alarm condition has been detected. If an alarm condition has not been detected, the method returns to the start (block 42). If an alarm condition has been detected, an alarm signal is emitted by one or multiple alarm indicators (e.g., speaker 12) in block 46 and an alarm timer is initiated in block 48. The alarm signal may include a tone emitted from a speaker, a vibration emitted from a pager, a light emitted from a display and so forth.

After an alarm has been initiated (block 46), the method 40 begins determining whether the alarm condition still exists and/or whether the alarm signal has been acknowledged, as illustrated by blocks 50 and 52. Specifically, block 50 is a decision block regarding whether a user has provided confirmation that the alarm condition has been recognized or acknowledged. Such an indication of acknowledgement may be provided by, for example, depressing the alarm silence button 16. If the alarm condition has been acknowledged, the unexpired alarm timer is reset or canceled (block 54) and an alarm silence timer may be initiated (block 56). In the illustrated embodiment, the alarm silence timer is then monitored, as illustrated by block 58. When the alarm silence timer expires, block 58 directs the method 40 to start again at block 42. In some embodiments, the alarm silence timer is not utilized. For example, in some embodiments, once a specific alarm is acknowledged, the same alarm condition will not initiate the primary alarm again, thus eliminating potentially unnecessary alarms. In other words, in such embodiments, the same alarm condition will not cause repeated alarm signals to be periodically emitted after acknowledgement when the alarm silence timer expires.

Block 52 is a decision block regarding whether the alarm condition still exists after being initiated. If the alarm condition is no longer present (e.g., the patient's blood pressure returns to normal), the alarm signal is canceled in block 60, the alarm timer is reset or canceled in block 62, and the method 40 begins again at block 42. For example, in one embodiment, if a patient's temperature passes a set point and then returns to normal the alarm will cease regardless of whether the alarm has been acknowledged. If the alarm condition remains present and has not been acknowledged, the alarm signal is continually emitted, the alarm timer continues to run, and the method 40 proceeds to block 64. It should be noted that in some embodiments, the presence of the alarm condition is not required to maintain the alarm. In other words, the method 40 proceeds without determining whether the alarm condition persists (block 52). For example, in some embodiments, the alarm remains active until acknowledged regardless of whether the alarm condition ceases to exist. This may be desirable in situations that benefit from requiring a user to be made aware that an alarm event occurred.

Block 64 is a decision block regarding whether the alarm timer has expired. If the alarm timer has not expired, the method 40 loops back to block 50. If the alarm timer has expired, a secondary alarm signal is emitted (block 66). As discussed above, this secondary alarm not only serves to increase awareness but also provides redundancy. In one embodiment, the secondary alarm signal has properties different than the primary alarm. For example, where the primary alarm is an audible tone, the secondary alarm may be an audible tone that is emitted with a higher frequency and/or a higher volume. Additionally, if the alarm timer has expired, the alarm timer may be reset with different properties (block 68). For example, the alarm timer may be reset with a reduced period (e.g., half of the initial alarm timer period). In some embodiments, this procedure continues as each successive alarm timer expires, thus gradually increasing communicated urgency, distinguishing features (e.g., type of sound), and/or the annoyance level of the alarm. Further, it should be noted that in some embodiments, acknowledging the alarm by, for example, pushing the alarm silence button 16, acknowledges and silences all alarms (e.g., both primary and secondary alarms).

Figure 3:
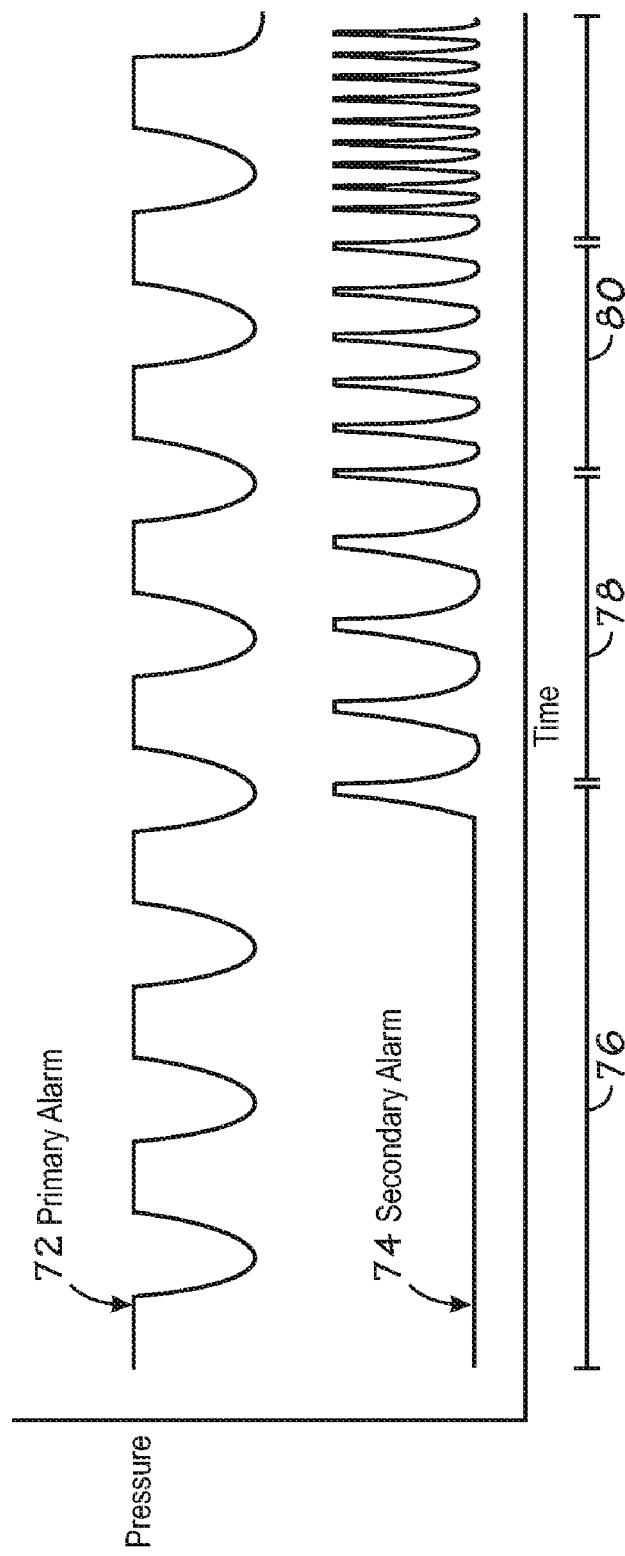
FIG. 3 is a pressure-time plot of a primary alarm signal and a secondary alarm signal in accordance with an exemplary embodiment of the present invention.

FIG. 3 is a pressure-time plot of a primary alarm signal and a secondary alarm signal in accordance with an exemplary embodiment of the present invention. While two signals are depicted in the illustrated embodiment, in some embodiments a plurality of signals may be utilized. Specifically, the plot 72 represents an audible signal or alarm emitted from the first speaker 12 as a primary alarm when an alarm condition is detected and unacknowledged. The plot 74 represents an audible signal or alarm emitted from the second speaker 14 as a secondary alarm when the primary alarm has remained unacknowledged for a predetermined amount of time. In some embodiments, a single speaker can be used to emit both alarms 72 and 74. It should be noted that while the illustrated alarms 72 and 74 have pulse waveforms, in other embodiments, the alarms 72 and 74 can have different waveforms (e.g., ramp wave, sine wave, triangle wave). Further, in some embodiments, the alarm signals are not audible but include other types of signals (e.g., vibrations from a pager). For example, in one embodiment, alarm signals are provided by a single or redundant set of vibratory transducers to provide further safety, versatility, and reliability.

As shown in FIG. 3, the secondary alarm 74 is silent during the initial alarm period and changes in frequency over time to increase annoyance, thus drawing attention to the unacknowledged alarm condition. In the illustrated embodiment, after the primary alarm 72 remains unacknowledged for a first amount of time 76, the secondary alarm 74 is initiated with a duty cycle that is interleaved with that of the primary alarm 72. After a second amount of time 78 (e.g., half of the primary time) beyond initiation of the secondary alarm 74, properties of the secondary alarm 74 are changed. Specifically, in the illustrated embodiment, the frequency of the alarm is increased, thus increasing annoyance. In other embodiments, different aspects of the primary and/or secondary alarms 72 and 74 are changed. For example, amplitude, duty cycle, frequency, and harmonic content can be manipulated over time to increase annoyance levels of all or some signals being emitted. In one embodiment, the alarms 72 and 74 begin sweeping through frequencies as the alarm condition remains unacknowledged. In the illustrated embodiment, the annoyance level is continually increased until it reaches a peak level or the alarm is acknowledged. For example, after a third amount of time 80 (e.g., half of the second time 78) beyond the second amount of time 78, the frequency of the secondary alarm 74 is changed again.

Figure 4:
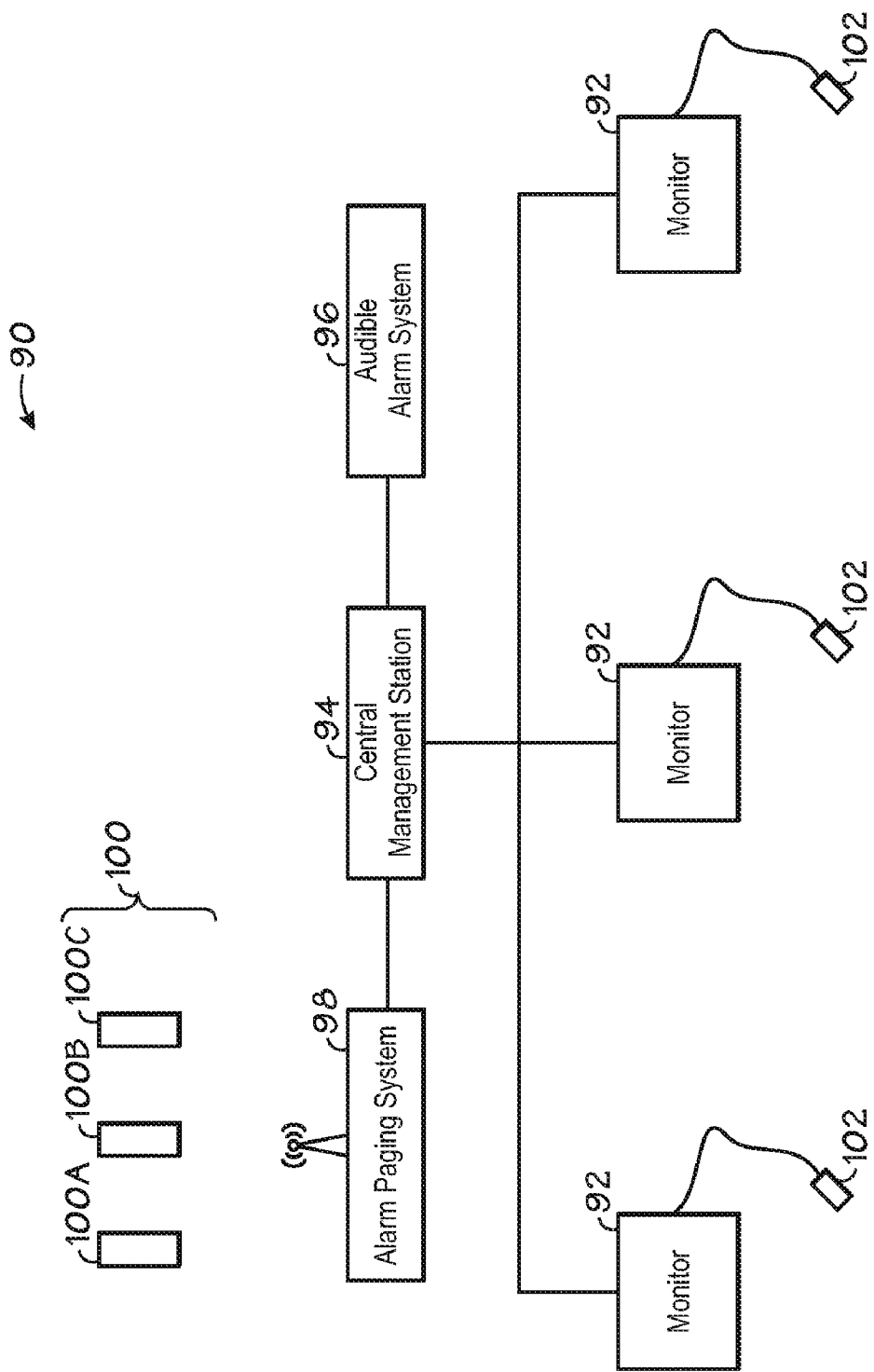
FIG. 4 is a block diagram of a monitoring system in accordance with an exemplary embodiment of the present invention.

FIG. 4 is a block diagram of a monitoring system in accordance with an exemplary embodiment of the present invention. Specifically, FIG. 4 illustrates a monitoring system 90 including a plurality of patient monitors 92 networked to a central management station 94 (e.g., a personal computer), which is coupled with an audible alarm system 96 and an alarm paging system 98. The alarm paging system 98 includes a set of wireless and mobile pagers 100. This monitoring system 90 facilitates monitoring multiple patients in, for example, a hospital or clinic. It should be noted that in some embodiments, the audible alarm system 96 and the alarm paging system 98 are included in the monitors 92. Further, it should be noted that in the illustrated embodiment, the monitoring system 90 is networked with network cables. However, in some embodiments, wireless communication is utilized.

Each of the patient monitors 92 includes a sensing device 102 (e.g., temperature sensor, pulse sensor) for measuring patient physiological data. Additionally, each of the monitors 92 or the central management station 94 is configured to alarm based on predefined physiological data values or conditions relating to such values. For example, an alarm may be activated when a patient's temperature has been at a certain level for a predefined amount of time.

When alarm conditions are detected, the system 90 emits alarm signals from the audible alarm system 96 and/or the alarm paging system 98. Further, as discussed above, if the alarm is not acknowledged, the monitoring system 90 increases the alarm annoyance level. For example, in the illustrated embodiment, a primary alarm signal is sent to a first pager 100A. If this primary alarm is not acknowledged within a predefined amount of time, a second alarm is sent to a second pager 100B. If the second alarm remains unacknowledged for a predefined amount of time (e.g., half of the time allotted to acknowledge the primary alarm), a third alarm is sent to a third pager 100C and so forth. Additionally, the annoyance level of each pager alarm may be increased. For example, the pagers may beep or vibrate with a higher amplitude and/or frequency. Further, audible alarms from a speaker or speakers of the audible alarm system 96 may substitute or supplement the pager alarms. Indeed, the audible alarm system 96 may emit audible alarm tones with increasingly annoying characteristics, as discussed above with regard to FIG. 3.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A pulse oximetry monitoring system, comprising:
a pulse oximeter including a plurality of built-in speakers, wherein the pulse oximeter comprises an alarm device configured to:
initiate a primary alarm through one of the plurality of built-in speakers in response to determining that a measurement of a physiological data value obtained by the pulse oximeter meets a defined requirement;
initiate a secondary alarm through another of the plurality of built-in speakers if an alarm acknowledgement mechanism is not activated prior to a first designated event; and
escalate a property of the secondary alarm if the alarm acknowledgement mechanism is not activated prior to a second designated event.

2. The system of claim 1, comprising the alarm acknowledgement mechanism.

3. The system of claim 2, wherein the alarm device is configured to emit the primary alarm at a first frequency and the secondary alarm at a second frequency when an alarm condition is recognized, the second frequency increasing if the alarm acknowledgement mechanism is not activated prior to the second designated event.

4. The system of claim 2, wherein the alarm device is configured to increase a magnitude of the secondary alarm if the alarm acknowledgement mechanism is not activated prior to the second designated event.

5. The system of claim 2, wherein the alarm device is configured to increase magnitudes of the primary and secondary alarms if the alarm acknowledgement mechanism is not activated prior to the second designated event.

6. The system of claim 5, comprising a timer configured to count down a first designated amount of time, wherein completion of the count down is the first designated event.

7. The system of claim 1, comprising a sensor configured to gather actual physiological data from a patient.

8. The system of claim 1, comprising a pager configured for wireless communication with the pulse oximeter and operation remote from the pulse oximeter.

9. A pulse oximeter, comprising:
an alarm detection device configured to measure physiological data received via the pulse oximeter, the alarm detection device configured to initiate an alarm in response to predefined measurements of the physiological data;
a first built-in speaker configured to emit a first signal with a first property; and
a second built-in speaker configured to emit a second signal with a second property, the first signal and the second signal being emitted when the alarm is initiated, and wherein the alarm detection device is configured to escalate the second property of the second signal if an alarm acknowledgement mechanism is not activated prior to a designated event.

10. The pulse oximeter of claim 9, wherein the first and second signals are different audible tones and the first and second properties are different frequencies.

11. The pulse oximeter of claim 9, wherein the pulse oximeter includes a pager system that is built into the pulse oximeter.

12. The pulse oximeter of claim 9, wherein the first property is manipulated if the alarm acknowledgement mechanism is not activated prior to the designated event.

13. The pulse oximeter of claim 9, comprising a plurality of external speakers directly coupled to the patient monitor via connection points.

14. The pulse oximeter of claim 9, comprising a first pager configured to be activated if the alarm acknowledgement mechanism is not activated prior to the designated event, and a second pager configured to be activated if the alarm acknowledgement mechanism is not activated prior to a second designated event.

15. A method for facilitating clinical vigilance, comprising:
receiving physiological data from a patient into a pulse oximeter;
measuring the physiological data with the pulse oximeter and initiating an alarm in response to predefined measurements of the physiological data;
emanating a first signal with a first property from a first built-in speaker of the pulse oximeter, and a second signal with a second property from a second built-in speaker of the pulse oximeter when the alarm is initiated; and
escalating the first property or the second property if an alarm acknowledgement mechanism is not activated prior to a designated event.

16. The method of claim 15, comprising escalating the first and the second property with the pulse oximeter if the alarm acknowledgement mechanism is not activated prior to a second designated event.

17. The method of claim 15, comprising emanating the first and second signals as different audible tones.

18. The method of claim 15, comprising emanating a third signal from a pager in remote communication with the pulse oximeter when the alarm is initiated.

19. The method of claim 15, wherein the first and second properties are different frequencies.

20. The method of claim 15, wherein the first and second properties are different volumes.

21. A pulse oximeter configured to receive blood oxygen saturation data from a patient, the monitor comprising:
an alarm detection device configured to measure the blood oxygen saturation data and initiate an alarm in response to a value of the blood oxygen saturation data meeting a criterion;
at least two speakers directly coupled with the pulse oximeter, the at least two speakers each configured to emanate a first signal and a second signal when the alarm is initiated; and
an alarm timer configured to start when the alarm is initiated and to reset with a reduced period if an alarm acknowledgement mechanism is not activated prior to a designated event, wherein said alarm detection device is configured to escalate a property of the first signal or the second signal upon completion of each period of the alarm timer.

22. The pulse oximeter of claim 21, comprising a paging system built-in to the pulse oximeter, wherein the paging system is configured to initiate a pager alarm if the alarm remains unacknowledged a designated amount of time after the alarm condition is detected.

23. The pulse oximeter of claim 21, wherein said alarm detection device is configured to cause a first speaker to emit a first audible sound and a second speaker to emit a second audible sound different from the first audible sound.

24. The pulse oximeter of claim 21, wherein said alarm detection device is configured to cause a first speaker to emit and maintain a first audible sound while an alarm condition is present and unacknowledged and a second speaker to emit a second audible sound that escalates over time while the alarm condition is present and unacknowledged.

25. The pulse oximeter of claim 21, wherein the at least two speakers are built-in speakers of the pulse oximeter.

* * * * *